(12) United States Patent
Wolyniec et al.

(10) Patent No.: US 8,156,785 B1
(45) Date of Patent: Apr. 17, 2012

(54) METHOD AND APPARATUS FOR DETERMINING A VALUE THAT CORRELATES TO AVAILABLE TRACTION

(76) Inventors: Larry Wolyniec, Darien, IL (US); Edward Litke, Tinley Park, IL (US)

( * ) Notice: Subject to any disclaimer, the term of this patent is extended or adjusted under 35 U.S.C. 154(b) by 518 days.

(21) Appl. No.: 12/415,810

(22) Filed: Mar. 31, 2009

(51) Int. Cl.
*G01N 3/62* (2006.01)
(52) U.S. Cl. .............................................. 73/9
(58) Field of Classification Search .............. 73/7, 9
See application file for complete search history.

(56) References Cited

U.S. PATENT DOCUMENTS

| | | | |
|---|---|---|---|
| 3,640,118 A * | 2/1972 | Geis | 73/9 |
| 5,113,688 A * | 5/1992 | Lazeration | 73/8 |
| 5,167,148 A * | 12/1992 | Black et al. | 73/121 |
| 5,569,117 A * | 10/1996 | Kono et al. | 477/169 |
| 6,460,398 B1 * | 10/2002 | Stopp et al. | 73/9 |
| 7,398,669 B2 * | 7/2008 | Mahajan et al. | 73/10 |
| 7,666,110 B2 * | 2/2010 | Iwatsuki et al. | 474/28 |
| 2007/0068220 A1 * | 3/2007 | Mahajan et al. | 73/9 |

* cited by examiner

*Primary Examiner* — John Fitzgerald
(74) *Attorney, Agent, or Firm* — Vedder Price, PC

(57) ABSTRACT

A method and apparatus for determining a value that correlates to available traction that is a lightweight, hand-held, portable apparatus that may include a pad of material, a translating assembly, a load assembly, a first device to move the pad and a second device that measures a peak amount of break-away torque. The load assembly facilitates application of a calibrated load to the pad as a result of but regardless of a force applied to the apparatus.

40 Claims, 4 Drawing Sheets

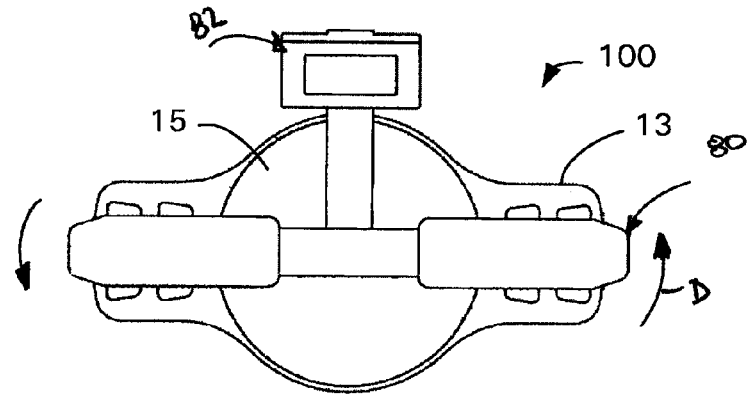
FIG. 3
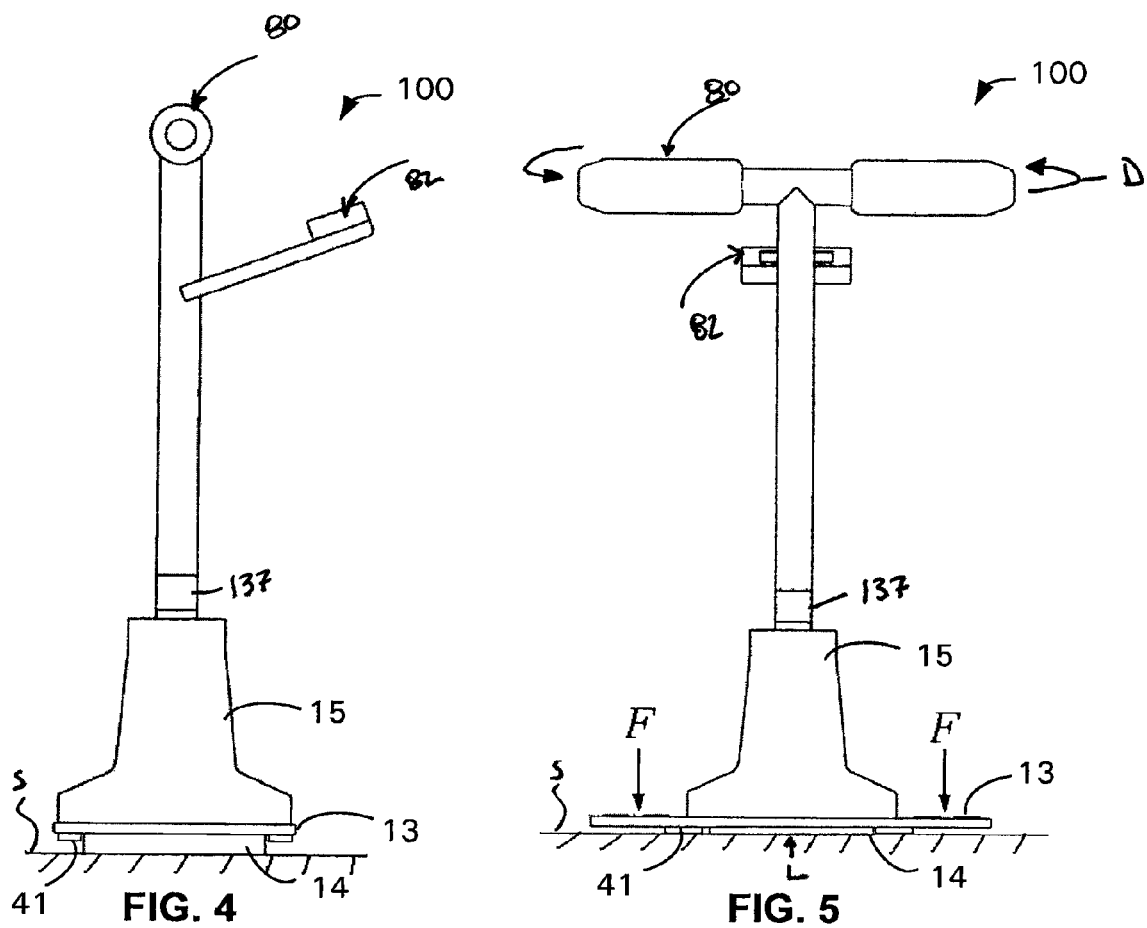
FIG. 4     FIG. 5

METHOD AND APPARATUS FOR DETERMINING A VALUE THAT CORRELATES TO AVAILABLE TRACTION

FIELD OF THE DISCLOSURE

The present disclosure generally relates to a method and apparatus for determining a value that correlates to available traction, and more specifically to a portable, hand-held device that applies a calibrated load to a pad in order to determine traction available, a method of use thereof and a method of determining available traction.

BACKGROUND

One of ordinary skill in the art recognizes that traction is most commonly defined as adhesive, static or, generally, any friction between a body and a surface on which the body is to move. The greater the traction, the greater the force that is required such that the body slides with respect to the surface, i.e. friction and hence traction is or approaches zero. For example, vehicle tires and a concrete surface define a certain traction value between them based on the physical composition and structural configuration of each of them in a complex manner that is beyond the scope of this disclose, but know to one of skill in the art by reference to applicable science and engineering texts. Loss of traction may happen when there is sliding between the body and the surface as a result of sufficient force and/or a different surface interposed between the body and the primary surface (such as, water, lubricant or other similar material).

Current known devices that are used to measure traction with respect to a road surface are disadvantageous in that they are large, bulky, unnecessarily complex, difficult to operate and expensive. Generally, a large, heavy and complex apparatus is towed or rolled over a given surface during use. Separate and/or shared hydraulic, electrical and/or electronic systems are commonly used in connection with an additional or separate wheel and tire combination, whereby traction between the tire and the surface may be determined by reference with respect to other wheels of the towing vehicle or the apparatus.

Accordingly, there is a need in the art for a lightweight, hand-held, portable device capable of determining a value that correlates to the available traction between a body and a desired surface.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. Certain embodiments are shown in the drawings. However, it is understood that the present disclosure is not limited to the arrangements and instrumentality shown in the attached drawings.

FIG. 3 is a top view of the apparatus of FIG. 1.

FIG. 4 is side elevation view of the apparatus of FIG. 1.

FIG. 5 is a front elevation view of the apparatus of FIG. 1.

SUMMARY

Figure 1:
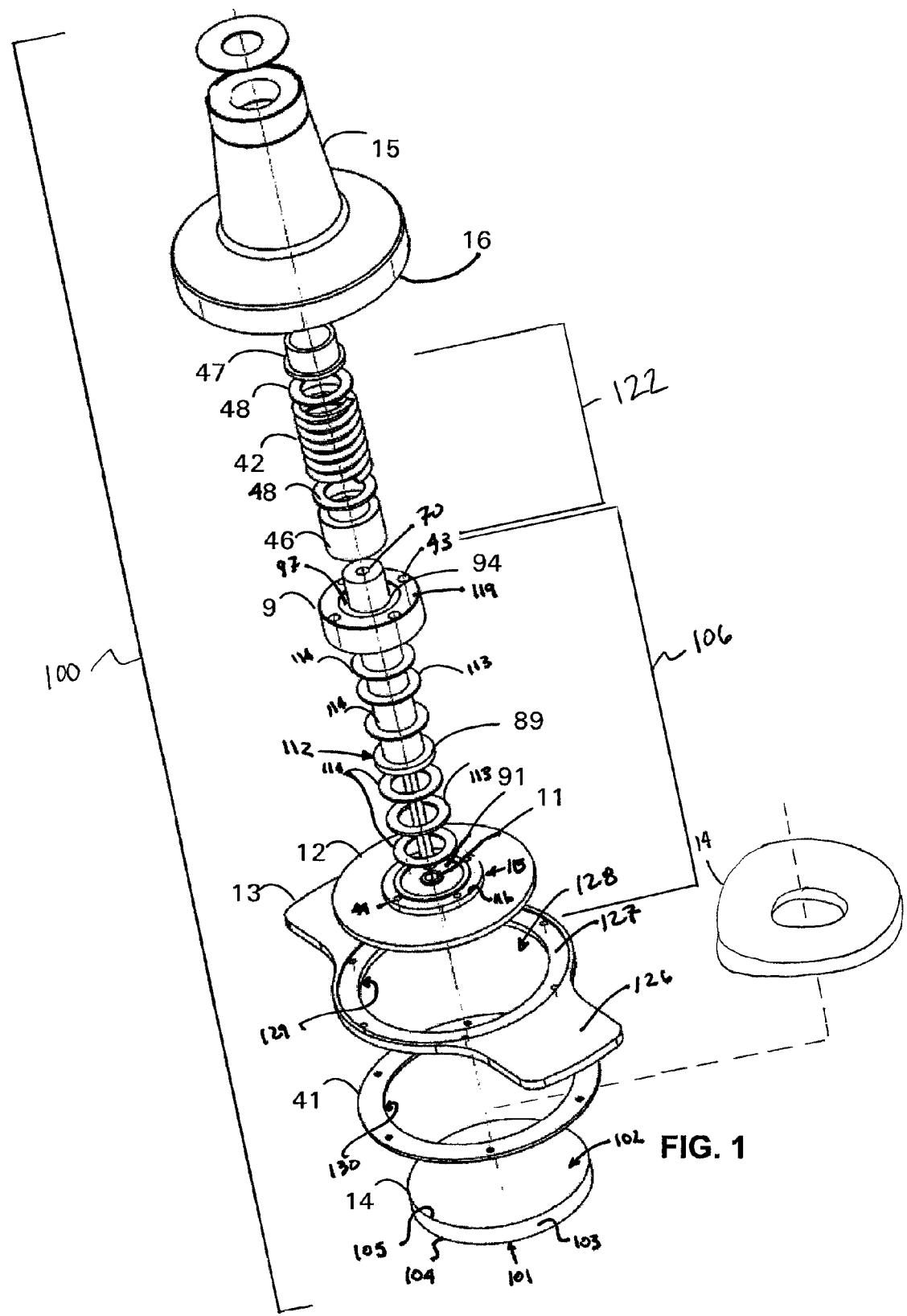
FIG. 1 is an exploded perspective view of a portable, hand-held apparatus for determining a value that correlates to available traction according to an embodiment of the present disclosure.

The present disclosure generally relates to a method and apparatus for determining a value that correlates to available traction that is a lightweight, hand-held, portable and may include a pad of material, a translating assembly, a load assembly, a first device to move the pad and a second device that measures a peak amount of break-away torque. The load assembly facilitates application of a calibrated load to the pad as a result of, but regardless of, a force applied to the apparatus.

More specifically, the present disclosure relates to a lightweight, hand-held, portable device capable of determining a value that correlates to the available traction between a body and a desired surface and a method of use thereof. The apparatus may include a housing, a cylindrical pad that is adapted to be moved with respect to the desired surface, a base connected to the housing for applying a force to the housing and consequently a calibrated load the pad via a biasing assembly, a first device that moves the pad and a second device that measures a peak amount of break-away torque. The housing and base are decoupled from the pad via the biasing assembly with a calibrating displacement so as to allow the base to rest on the ground and transfer only a calibrated portion of the force or a predetermined load on the base to the pad.

One aspect of the present disclosure relates to an apparatus for determining a value that correlates to available traction comprising a pad of material, a first device operatively connected to the pad that moves the pad relative to a desired surface, wherein the pad includes a planar first major surface disposed contiguous with the desired surface, and a second device operatively connected to the first device that measures a peak amount of break-away torque.

Another aspect of the present disclosure relates to an apparatus for determining a value that correlates to available traction comprising a pad having a first major surface and a second major surface. A bracket is connected to the second major surface of the pad and includes a bore and a bearing surface. An outer shaft includes a through-bore and an annular flange having an upper section and a lower section. An inner shaft slidably engages the bore at one end and the through-bore at another end. A first bearing assembly is disposed contiguous with the bearing surface and the lower section. A second bearing assembly disposed contiguous with the upper section. A cap is connected to the bracket and includes an inner surface, an opening and a spring pad. The inner surface of the cap is disposed contiguous with the second bearing assembly. A biasing assembly is disposed contiguous with the spring pad. A housing including an inner surface is disposed contiguous with the biasing element. A first device is connected to the through-bore. A second device is operatively connected to the first device to measure a peak amount of break-away torque.

Yet another aspect of the present disclosure relates to an apparatus for applying a calibrated load to a pad for determining a value that correlates to available traction comprising a pad of material, a first device operatively connected to the pad that moves the pad relative to a desired surface, wherein the pad includes a planar first major surface disposed contiguous with the desired surface, and a second device operatively connected to the first device that measures a peak amount of break-away torque.

Still another aspect of the present disclosure relates to a method of determining a value that correlates to available traction comprising moving a pad of material relative to a desired surface, wherein the pad includes a planar first major surface disposed contiguous with the desired surface, and measuring a peak amount of break-away torque.

DETAILED DESCRIPTION OF THE PREFERRED EMBODIMENTS

For the purposes of promoting and understanding the principles disclosed herein, reference is now made to the preferred embodiments illustrated in the drawings, and specific language is used to describe the same. It is nevertheless understood that no limitation of the scope of the disclosure is hereby intended. Such alterations and further modifications in the illustrated devices and such further applications of the principles disclosed and illustrated herein are contemplated as would normally occur to one skilled in the art to which this disclosure relates.

Figure 2:
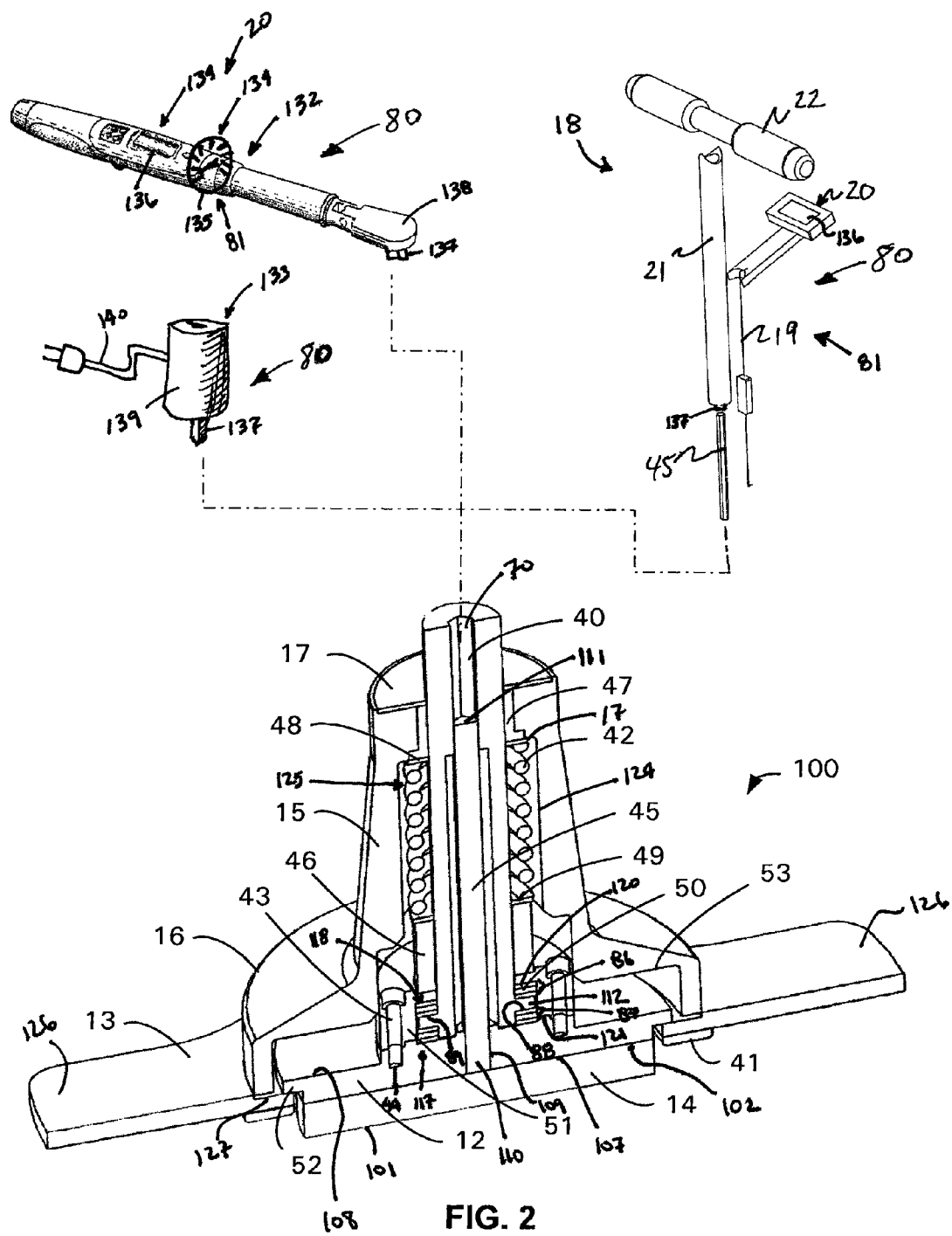
FIG. 2 is a cross sectional view of the apparatus of FIG. 1.

FIG. 1 shows an exploded perspective view of a portable, hand-held apparatus 100 for determining a value that correlates to available traction according to an embodiment of the present disclosure and FIG. 2 is a cross sectional view of the apparatus shown in FIG. 1. The apparatus 100 includes a pad 14 of material having a first major surface 101 and a second major surface 102. Generally, a major surface is defined as a surface of an object that has a greater area than a minor surface of the object. With respect to the pad 14, one of ordinary skill in the art will recognize that the first major surface is defined by a first outer diameter 104, the second major surface is defined by a second outer diameter 105, that the first and second outer diameters 104, 105 are equivalent in this embodiment and that there is one minor surface 103 of the pad 14 defined between the first and second outer diameters 104, 105. In one embodiment, preferably the first major surface 101 of the pad 14 has an area in the range of approximately 10 to 17 square inches.

The pad 14 may be configured to have any desirable shape, such as a disc, ring, parallelogram, triangle, oval, obround or any other geometry or shape. One of the advantages of using a pad that is configured symmetrical about its geometric central axis, such as a disc, ring or other like shape, is the ability to apply a uniform compression force upon the entire first major surface. Furthermore, the pad 14 may be formed for any suitable material, such as a natural material, synthetic material, polymer, elastomer, rubber, polyurethane or any other suitable or like material. One of ordinary skill in the art will recognize that the choice of material that is used for the pad 14 may be advantageous with respect to the measurement or the desired surface S on which the apparatus 100 will be used. Preferably, in one embodiment the durometer of the pad 14 is in the approximate range of 40 to 80 Shore A. In other embodiments, the durometer may be outside the indicated range or within another range that may be advantageous with respect to the measurement or the desired surface S on which the apparatus 100 will be used. It will be recognized by one of ordinary skill in the art that the durometer of the pad 14 may be selected such that it is relative to the desired surface S or would produce the most accurate or repeatable results. For example, it has been found that a pad 14 made of a rubber material having a disc shape, a thickness of approximately one half inch, an outer diameter of approximately four and one half inches, honed-flat substantially planar first and second major surfaces and a durometer of approximately 70 Shore A delivers exceptionally accurate and repeatable results when used with the apparatus 100 in connection with concrete and asphalt surfaces. Additionally, if a user of the apparatus 100 desires to measure the traction between a portion of road and a rubber tire, the material of the pad 14 may be a flat rubber surface or a flattened portion of a rubber tire having grooves and surface asperities.

A translating assembly 106 may be provided for translating movement of the first device 80 (see FIG. 2) to the pad 14. The translating assembly 106 may include a bracket 12, an inner shaft 45, an outer shaft 40, a first bearing assembly 87, a second bearing assembly 86 and a cap 9. The bracket 12 includes a bottom portion 107 and a top portion 108. Preferably, the bracket 12 is formed from a lightweight material, such as, for example 6061 Aluminum. One of ordinary skill in the art will recognize that the bracket 12 may also be formed of any other suitable material that achieves the desired purpose and result, such as, for example only, metal, plastic, composite materials, titanium, steel or other like materials. The bottom portion 107 is configured generally planar and is adapted for connection to the pad 14. In a preferred embodiment, the pad 14 is connected to the bottom portion 107 by a structural adhesive. One of ordinary skill in the art will recognize that any method or manner of connecting the pad 14 to the bottom portion 107 is anticipated, including, without limitation, mechanical fasteners, registration slots and other know connection apparatus. The top portion 108 has an outer diameter that is larger than the outer diameter of the bottom portion 107, as seen in FIG. 2, for preventing the apparatus 100 from falling apart as further detailed below. Additionally, the top portion 108 includes a bore 109 and a bearing surface 91 defined and formed therein. The bore 109 is aligned with the geometric central axis of the bracket 12. Preferably, the bore 109 is configured to have a complementary shape to the inner shaft 45 whereby there is positive registration between the two parts. For example, in the embodiment shown in FIG. 1, the bore 109 is configured as a 5/16" hexagon through bore. One of ordinary skill in the art will recognize that any other geometry that provides complementary positive registration between the two parts is anticipated, such as, but not limited to, squares, multi-sided shapes, splines and other configurations that matingly engage, interdigitate or otherwise mesh together to translate movement. Additionally, the bore 109 may be a blind bore that does not extend through the thickness of the bracket 12. The bearing surface 91 is defined about the bore 109 as a generally flat surface on which a bearing assembly may be contiguous. Preferably, in one embodiment, the bearing surface 91 is concentric about the geometric central axis of the bracket 12. In another preferred embodiment, the bearing surface 91 may be formed on a raised section 115 of the bracket 12 that defines a registration shoulder 116 as will be defined in more detail below with respect to the cap 9.

The inner shaft 45 operatively engages the pad 14 at one end 110 and the outer shaft 40 at another end 111. For example, the inner shaft 45 may slidably engage the bore 109 at one end 110 and slidably engage a through-bore 70 of the outer shaft 40 at another end 111. In one embodiment, one end 110 of the inner shaft 45 is connected to the bracket 12 by complementary positive registration engagement with the bore 109. In such embodiment, both are hexagonal-shaped to permit a slight tolerance fit. The geometric configuration of the inner shaft 45 need not be continuous over the length of the inner shaft 45. For example, the inner shaft 45 may have hexagonal-shaped ends and a cylindrical or round shaped mid-section. One of ordinary skill in the art will recognize that other possible combinations from know configurations are possible. One important advantage of the apparatus 100 is that the inner shaft 45 provides consistent performance. In one embodiment, it has been found that titanium is an excellent material of construction because of its physical properties. One of ordinary skill in the art will recognize that any other suitable material of construction may be used for the inner shaft 45, such as, for example only, steel, aluminum, composite compositions, plastics, metals and other like materials.

The outer shaft 40 includes the through-bore 70 and an annular flange 60. The through-bore 70 is aligned with the geometric central axis of the outer shaft 40. Preferably, the through-bore 70 is configured to have a complementary shape to the inner shaft 45 whereby there is positive registration between the two parts. For example, in the embodiment shown in FIG. 1, the through-bore 70 is configured as a $5/16$" hexagon bore. One of ordinary skill in the art will recognize that any other geometry that provides complementary positive registration between the two parts is anticipated, such as, but not limited to, squares, multi-sided shapes, splines and other configurations that matingly engage, interdigitate or otherwise mesh together to translate movement. Additionally, the through-bore 70 may be a blind bore that does not extend through the length of the outer shaft 40. Preferably, the bracket 12 is formed from a lightweight material, such as, for example 6061 Aluminum. One of ordinary skill in the art will recognize that the bracket 12 may also be formed of any other suitable material that achieves the desired purpose and result, such as, for example only, metal, plastic, composite materials, titanium, steel or other like materials. The annular flange 60 is formed on the outer shaft 40 and has an upper section 89, a lower section 88 and an annular margin 112 defined therebetween.

A first bearing assembly 87 and second bearing assembly 86 generally include any collection of parts necessary to provide substantially friction-free rotation or angular movement of the outer shaft 45 with respect to the bracket 12. Preferably, each bearing assembly 87, 86 may include a plurality of components including bearings 113 and washers (or spacers) 114. In one embodiment each bearing assembly 87, 86 may include a bearing 113 and a pair of washers 114 disposed on opposite sides of the bearing 113, the washers 114 are useful to set the desired tolerance or play (and hence friction) with respect to the rotation or angular movement of the outer shaft 40. The tighter the tolerance the more friction with respect to the rotation or angular movement of the outer shaft 40 relative to the bracket 12. Likewise in opposition, a very loose tolerance will allow too much unwanted movement of the outer shaft 40. In one preferred embodiment, the pair of washers 114 each has a thickness of 0.186 inches. One of ordinary skill in the art will recognize that a bearing that has an outer diameter and an inner diameter and provides bearing elements that allow generally flat surfaces to move with respect to one another is preferred. For example, the bearing may be a Torrington bearing, such as, in a preferred embodiment, for example only, part number TRb1625. Moreover, the washer (or spacer) 114 may be made from aluminum, metal, composite material, plastic, steel or any other suitable material. Additionally, it is within the teachings of the present disclosure that each bearing assembly 87, 86 may include a pair of bearings 113 with a singular or set of washers 114 between the pair of bearings 113. One of ordinary skill in the art will recognize that a proper stack height and/or tolerance with respect to the applicable parts (bracket 12, cap 9 and annular flange 112) are necessary to achieve accurate and repeatable operation of the apparatus 100. Additionally, one of ordinary skill in the art will recognize that each of the above identified parts may be considered variables that can be adjusted in dimension to achieve the desires purpose and results and that this disclosure is not limited to any embodiment shown or described herein.

A cap 9 is configured for connection to the bracket 12 and includes a chamber 117, an opening 94 and a spring pad 97. In one embodiment, threaded fasteners (not shown for the sake of clarity) are inserted through the bores 43 in the cap to engage mating threaded bores 44 formed in the bracket 12. One of ordinary skill in the art will recognize that any suitable method or manner of connection the cap 9 to the bracket 12 may be used and is contemplated. For example, a press fit, structure adhesive and quick release fasteners represent only a limited few known alternatives that may be substituted. The chamber 117 is defined by an interior surface 118 of the cap 9. The interior surface 118 may have various elements or portions. For example, there may be an upper surface 120 and registration recess 121 defined in the interior surface 118. In one embodiment, the registration recess 121 may be configured to engage the registration shoulder 116 so that the cap is properly centered with respect to the bracket 12 (and the bore 109 and bearing surface 91). One of ordinary skill in the art will recognize that other known methods and manners for accurately centering two parts with respect to one another is within the teachings of this disclosure. The spring pad 97 is defined on an outer surface 119 of the cap 9. Preferably, the spring pad 97 is formed concentrically about the geometric central axis of the cap 9. In one embodiment, the spring pad 97 may be formed as a recess so as to enable the biasing assembly 121 to remain centered with respect to the geometric central axis of the apparatus 100. One of ordinary skill in the art, will recognize that the spring pad 97 may tale any suitable configuration. The opening 94 extends from the interior surface 118 to the exterior surface 119. Preferably, the bracket 12 is formed from a lightweight material, such as, for example 6061 Aluminum. One of ordinary skill in the art will recognize that the cap 9 may also be formed of any other suitable material that achieves the desired purpose and result, such as, for example only, metal, plastic, composite materials, titanium, steel or other like materials. Additionally, the opening 94 is preferably larger than an outer diameter of the outer shaft 40.

When the translating assembly 106 is assembled, as shown in FIG. 2, the first bearing assembly 87 is contiguous with the bearing surface 91 and the lower section 88 and the second bearing assembly 86 is contiguous with the upper section 89 and an interior surface 118 of the cap 9 with the proper tolerances as discussed above. As a result, the translating assembly 106 operates substantially friction-free. One of ordinary skill in the art will recognize that any other suitable material of construction may be used for the cap 9, such as, for example only, steel, composite compositions, plastics, metals and other like materials.

A biasing assembly 122 generally describes any suitable device, apparatus or assembly that is useful to apply a calibrated load on the pad 14 regardless of the force that is applied to a force assembly 123 (described in detail below). Preferably, the biasing assembly 122 is disposed contiguous with the spring pad 97 and the force assembly 123, and may include a biasing element 42, a spacer 46 and washers 48. In one embodiment, the biasing element 42 may be a coil spring as shown in FIGS. 1 and 2. In another embodiment, the coil spring may be referred to as a compression spring having an outer diameter of approximately 1 and one half inches, a wire thickness of approximately 0.190 inches and an length of approximately 2.3 inches. However, it is within the teachings of this disclosure that the biasing element 42 may be an air spring, a solenoid, a helix or screw drive device or a drive motor (all not shown for clarity, but known as conventional alternatives and substitutes) and the coil spring may have any other suitable dimensions in order to produce the desired result or purpose. One of ordinary skill in the art will recognize that any one of the foregoing may be easily substituted for the other and achieve the same purpose of transferring a predetermined load from the force assembly 123 to the pad 14.

The force assembly 123 generally describes any suitable device, apparatus or assembly that is useful to apply a force F to the biasing assembly 122. Preferably, the force assembly 123 may include a housing 15 connected to a base 13. The housing 15 may include a chamber 125 that is defined by an inner surface 124 that may include various portions or elements. For example, the inner surface 124 may include an inner shoulder 17 formed so as to be contiguous with the biasing assembly 122 (see FIG. 2). Additionally, the housing 15 may include a bottom portion 16 that defines an opening of the chamber 125. The bottom portion 16 may include any suitable method or manner for secure connection of the base 13 to the housing 15, such as, for example only, threaded fasteners, a press fit, structure adhesive and quick release fasteners represent only a limited few known alternatives that may achieve the desired purpose or result. The base 13 may include flanges 126 that facilitate application of a force F to the housing 15 and biasing assembly 122, whereby a user stepping or standing thereon (represented by the arrows with reference letter F shown in FIG. 5) may overcome the biasing element 42 in order to apply a calibrated load to the pad 14. One of ordinary skill in the art will recognize that the base 13 may be configured in an manner to achieve the desired purpose or result with respect to the associated components. For example, the housing 15 and base 13 may be configured dimensionally different than as shown in the event a coil spring is not used as the biasing element 42. Nevertheless, all such alternative constructions are contemplated by this disclosure. The base 13 may also include a recessed portion 127 that may be useful with respect to connection of the housing 15 to the base. Additionally, the base 13 may include an opening 128 defined by an inner diameter 129 and disposed about a geometric central axis of the base 13. In one embodiment, the bracket top portion 108 overlaps the inner diameter 129 (see FIG. 2) such that the bracket top portion 108 cannot extend past the inner diameter 129. Preferably, the housing 15 and base 13 are formed from a lightweight material, such as, for example 6061 Aluminum. One of ordinary skill in the art will recognize that the housing 15 and base 13 may also be formed of any other suitable material that achieves the desired purpose and result, such as, for example only, metal, plastic, composite materials, titanium, steel or other like materials.

In one embodiment, a load ring 41 may be connected to the base 13. Preferably, the load ring 41 has an inner diameter 130 that is generally larger than the first and second outer diameters 104, 105 of the pad 14. The load ring 41 concentrates contact of the force assembly 123 with the desired surface S and provides a vertical clearance for the flanges 126 above the desired surface S, in the event such a base 13 is used, to account for the scenario where the desired surface S only has a limited generally flat portion that generally corresponds in approximate dimension to the pad 14. One of ordinary skill in the art will recognize that the load ring 41 may be configured in any manner to achieve the desired purpose or result as set forth herein. Preferably, the load ring 41 is formed from a lightweight material, such as, for example 6061 Aluminum. One of ordinary skill in the art will recognize that the load ring 41 may also be formed of any other suitable material that achieves the desired purpose and result, such as, for example only, metal, plastic, composite materials, titanium, steel or other like materials.

In operation, a user steps on the base 13, overcoming the biasing element, whereby the force assembly 123 moves with respect to the pad 14 until the load ring 41 contacts the desired surface S thus calibrating the load on the pad 14 to the value of the calibrated load created by the biasing element 42. For example, if a force of 100 lb must be placed on the pad 14 to obtain accurate and repeatable results and a user with a weight of 240 lb steps on the base 13, the housing 15 will push down on the biasing element 42 and will compress the biasing element 42 until the load ring 41 touches the ground. The biasing element 42 will then push on the pad 14 with a fixed force calibrated as the movement of the plate in the housing 15 times the coefficient of the biasing element. Any residual weight or force from the user will be transferred via the load ring 41 to the desired surface.

A load assembly 131 generally describes the combination of the biasing assembly 122 and the force assembly 123 which, in combination, cooperate to apply a calibrated load to the pad 14 as a result of a force F applied to the apparatus 100 (see FIGS. 2, 4 and 5). Preferably, in one embodiment, the load is in the approximate range of 60 to 100 pounds force. One of ordinary skill in the art will recognize that the desirable range may be different depending on the desired surface, composition of the pad material and a host of various other factors. Additionally, it is within the teachings of the present disclosure that the range of the load may be selected to correspond to such factors and the numerical range indicated above shall not be so limited.

As shown in FIGS. 2-5, a first device 80 generally describes any device, apparatus or assembly that may be operatively connected to the pad 14 to move the pad 14 relative to the desired surface S. Preferably, the first device 80 may be a lever arm 18, a wrench 132 or a motor 133. One of ordinary skill in the art will recognize that any suitable device, apparatus or assembly that can impart rotational or angular movement and can be configured to be operatively connected to the pad 14 is within the teachings of this disclosure. In one embodiment, the first device 80 is connected to the translating assembly 106. In a more specific embodiment, the first device 80 is removably engages the through-bore 70 in a manner like the inner shaft 45 engages the outer shaft 40 or the bore 109, as described above, namely with any other geometry that provides complementary positive registration between the two parts, such as, but not limited to, squares, hexagons, multi-sided shapes, splines and other configurations that matingly engage, interdigitate or otherwise mesh together. Additionally, the first device 80 may be removably connected to the through-bore 70. In one embodiment, the lever arm 18 includes an upright 21 and a handle 22 disposed at a distal end. The upright 21 may include an interface projection 137 to facilitate removable connection with the through-bore 70. In another embodiment, the wrench 132 includes a head 138 and a handle 22. The head 138 may include an interface projection 137 to facilitate removable connection with the through-bore 70. In another embodiment, the motor 133 includes a body 139 and a power source 140. One of ordinary skill in the art will recognize that the motor may be any conventional design that is desirable and the power source may be a line source (120 or 240V for example), battery or solar power. The body 139 may include an interface projection 137 that extends from or is operatively connected to a rotating center element of the motor 133 to facilitate removable connection with the through-bore 70.

A second device 81 generally describes any device, apparatus or assembly that may be operatively connected to the first device 80 that measures a peak amount of break-away torque. In making such a measurement, the peak amount of break-away torque is determined as the highest torque reading that is achieved as measured from the second device 81. For example, in measuring the peak amount of break-away torque, the apparatus 100 is started from a static position. After a calibrated load has been applied to the pad 14, a user can move the first device 80 and in turn the pad 14 which is operatively connected thereto. As the first device is gradually moved the torque measured by the second device 81 (and hence the traction available between the pad and the desired surface) will continue to increase until a maximum or peak amount is reached. Thereafter, the pad 14 will break traction with the desired surface as will be noticed by an appreciable drop in measurable torque. The point at which the peak amount of torque is measure before the appreciable drop is the peak amount of break-away torque.

In one embodiment, the second device 81 may include a strain gauge 19 or a torque wrench gauge 134. One of ordinary skill in the art will recognize that each gauge described above 19, 134 requires more elements than are shown in order to function. However, for the sake of clarity, those details have not been reproduce herein because such knowledge is within the skill of one of ordinary skill in the art or would be readily obtainable without undue research. In particular, the torque wrench gauge 134 includes the mechanisms within or on the handle of a torque wrench that enable a user to determine a desired amount of to apply or which has been applied. Alternatively, in this disclosure, as will be described in more detail below, the torque wrench gauge 134 will measure a peak amount of break-away torque. For example, the torque wrench may be a mechanism design (beam type, deflecting beam type, click type, dial type, no hub type) or an electronic design (electronic torque/angle wrench, mechatronic type). Additionally, the strain gauge 19 in one embodiment may have an insulating flexible backing which supports a metallic foil pattern. The gauge 19 is attached to the inner shaft 45 by a suitable adhesive. As the inner shaft 45 is deformed, the foil is deformed, causing its electrical resistance to change. This resistance change, usually measured using a Wheatstone bridge, is related to the strain by the quantity known as the gauge factor. For measurements of small strain, semiconductor strain gauges, so called piezoresistors, are often preferred over foil gauges. A semiconductor gauge usually has a larger gauge factor than a foil gauge. However, semiconductor gauges tend to be more expensive, more sensitive to temperature changes, and are more fragile than foil gauges. Generally, the strain gauge 19 is preferably used with the lever arm 18 and the motor 133, but may also be used with the torque wrench 132 if so desired.

A display 20 generally describes any device, apparatus or assembly that may be operatively connected to the second device 81 for displaying a value that may be the peak amount of break-away torque or a traction value that correlates to the peak amount of break-away torque. Preferably, the display 20 is analog 135 or digital 136, depending on the type of second device 82 used per application. Again, as with respect to certain specifics of the second device 81, certain aspects of the display 20 is conventional knowledge to one of ordinary skill in the art or readily obtainable without undue research and will not be repeated or detailed herein. An analog display 135 may be a dial type that has a "tattle tale" feature which shows the peak value reached. Such value may be the amount of break-away torque, such as for example, a measurement of inch-pounds or foot-pounds. Alternatively, the value may be a traction value that correlates to the peak amount of break-away torque. In other words, an easier to read display may show high, medium high, medium, medium low and low ranges of traction. If the display falls in one of the above ranges the user will have a general idea of the amount of traction available. Likewise, the digital display 136 may be a liquid crystal or light emitting display or any other suitable or know display apparatus or assembly that shows an actual peak amount of break-away torque value or a traction value that correlates to the peak amount of break-away torque, as described above. One of ordinary skill in the art will recognize that other components may be required for the digital display 136 to function as described and that such components (for example, processor, circuits, electronic components, etc.) are well known or easily obtainable without undue experimentation.

A memory M generally describes any device, apparatus or assembly that may be operatively connected to the second device 81 or the display 20 for storing the data obtained, such as, for example, the peak amount of break-away torque values, a traction value that correlates to the peak amount of break-away torque or correlation tables for relation of the peak break-away torque value to a different traction value, amongst other data the user might be interested in storing with respect to the test, conditions, date, time, etc. The memory and the processor as described above are also connected to the power source, when needed such as for example a portable battery, solar or line voltage.

FIGS. 3-5 illustrate various views of the apparatus of FIG. 1 in operation. FIG. 3 is a top view of the apparatus 100 in a first operative position. FIG. 4 is a side elevation view of the apparatus 100 in the first operative position. Generally, the first operative position is described as the planar first major surface of the pad 14 is disposed contiguous with the desired surface S and no force has been applied. One important aspect of the first operative position is selecting a generally flat portion of the desired surface that generally corresponds in approximate dimension to the pad 14. In doing so, the user can take a more accurate measurement.

FIG. 5 is a front elevation view of the apparatus in a second operative position where a force F has been applied to the load assembly 131, such as by the feet of a user or any other method or manner as described herein. As a result, a predetermined calibrated load L is applied to the pad 14. The first device 80 may then be moved in the direction indicated by the arrows D, which in turn moves the pad 14 relative to the desired surface S because the pad 14 is operatively connected to the first device 80. The movement of the first device may be characterized as rotational or angular displacement which is normal to the desired surface.

Figure 6:
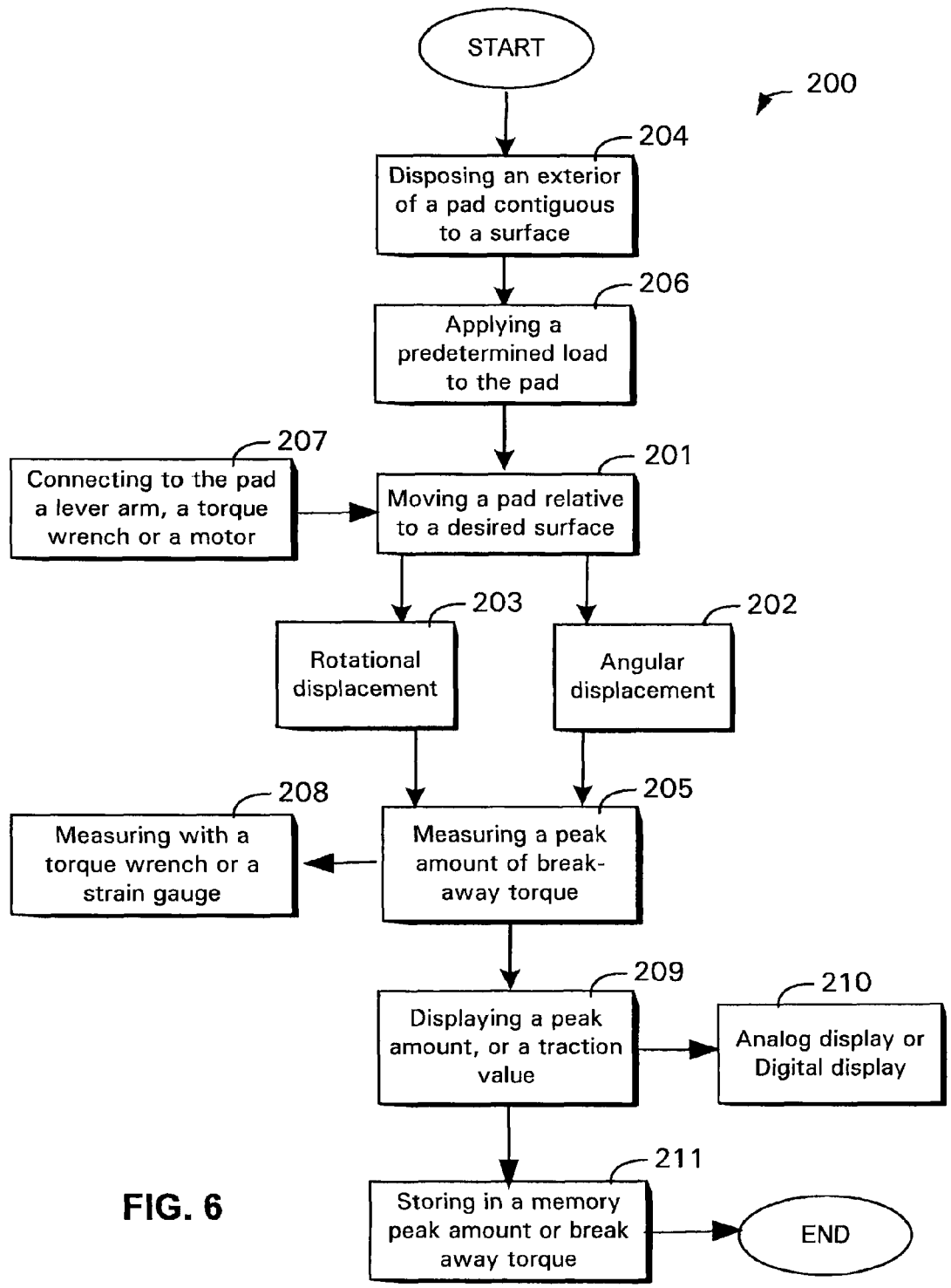
FIG. 6 is a functional diagram illustrating the different steps associated with a method of determining a value that correlates to available traction according to an embodiment of the present disclosure.

FIG. 6 illustrates, in a functional diagram, the different steps associated with a method of determining a value that correlates to available traction according to an embodiment of the present disclosure. A method 200 of determining a value that correlates to available traction comprises the steps of moving 201 a pad of material relative to a desired surface, where the pad includes a planar first major surface disposed contiguous with the desired surface, and measuring 205 a peak amount of break-away torque. The step of moving 201 may be selected from the group consisting of a rotational displacement 203 or an angular displacement 202 of the pad 14. The step of moving 201 may also include the step of operatively connecting 207 the pad to a first device. The step of moving 201 may further include the step of applying a predetermined load to the pad 206. The step of applying 206 may also include the step of selecting a generally flat portion of the desired surface that generally corresponds in approximate dimension to the pad 204.

The step of measuring 205 may be performed by the selection step 208 of a tool such as a torque wrench gauge or a strain gauge. In another embodiment, the method further includes the step of displaying 209 either a peak amount of break-away torque or a traction value that correlates to the peak amount of break-away torque. The step of displaying 209 can be performed 210 by either an analog display or a digital display. Finally, in yet another subsequent step, the values obtained at step 209 may be stored 211 into a memory.

It is understood that the preceding detailed description of some examples and embodiments of the present invention may allow numerous changes to the disclosed embodiments in accordance with the disclosure made herein without departing from the spirit or scope of the invention. The preceding description, therefore, is not meant to limit the scope of the invention but to provide sufficient disclosure to one of ordinary skill in the art to practice the invention without undue burden.

What is claimed is:

1. A method of determining a value that correlates to available traction comprising:
   applying a predetermined load directly to a pad of material with a load assembly which includes a biasing assembly;
   moving the pad of material relative to a desired fixed surface, wherein the pad includes a first major surface disposed contiguous with the desired surface; and
   measuring a peak amount of break-away torque.

2. The method of claim 1, wherein the step of moving is selected from the group consisting of rotational displacement and angular displacement.

3. The method of claim 1, wherein the first major surface has an area in the approximate range of 10 to 17 square inches.

4. The method of claim 1, further comprising selecting a generally flat portion of the desired fixed surface that generally corresponds in approximate dimension to the pad.

5. The method of claim 1, wherein the load assembly further includes a force assembly.

6. The method of claim 1, wherein the load is in the approximate range of 60 to 100 pounds force regardless of a force applied by a force assembly.

7. The method of claim 1, wherein the step of moving further comprises operatively connecting to the pad to a selected one from the group consisting of a lever arm, a torque wrench and a motor.

8. The method of claim 1, wherein the step of measuring is selected from the group consisting of a torque wrench gauge and a strain gauge.

9. The method of claim 1, further comprising storing in a memory selected from one of the group consisting of the peak amount of break-away torque and a traction value that correlates to the peak amount of break-away torque.

10. The method of claim 1, further comprising displaying a selected one from the group consisting of the peak amount of break-away torque and a traction value that correlates to the peak amount of break-away torque.

11. The method of claim 10, wherein the step of displaying is selected from the group consisting of an analog display and a digital display.

12. An apparatus for determining a value that correlates to available traction comprising:
   a pad of material including a first major surface;
   a first device operatively connected to the pad that moves the pad relative to a desired surface;
   a second device operatively connected to the first device that measures a peak amount of break-away torque; and
   a load assembly for applying a load to the pad, including a force assembly and a biasing assembly.

13. The apparatus of claim 12, wherein the pad material is selected from the group consisting of natural material, synthetic material, polymer, elastomer, rubber and polyurethane.

14. The apparatus of claim 12, wherein the pad of material has a durometer in the approximate range of 40 to 80 Shore A.

15. The apparatus of claim 12, wherein the pad of material has a durometer that is relative to the desired surface.

16. The apparatus of claim 12, wherein the first device is selected from the group consisting of a lever arm, a torque wrench and a motor.

17. The apparatus of claim 12, wherein the second device is selected from the group consisting of a torque wrench gauge and a strain gauge.

18. The apparatus of claim 12, further comprising a memory for storing one selected from the group consisting of the peak amount of break-away torque and a traction value that correlates to the peak amount of break-away torque.

19. The apparatus of claim 12, wherein the biasing assembly includes a biasing element that is selected from the group consisting of a coil spring, an air spring, a solenoid, helix drive or drive motor.

20. The apparatus of claim 12, wherein the force assembly includes a housing and a base to facilitate application of a force sufficient to overcome a biasing element of the biasing assembly.

21. The apparatus of claim 12, wherein the pad has a configuration selected from the group consisting of a disc, a ring and a shape symmetrical about a geometric central axis.

22. The apparatus of claim 12, further comprising a display operatively connected to the second device for displaying a selected one from the group consisting of the peak amount of break-away torque and a traction value that correlates to the peak amount of break-away torque.

23. The apparatus of claim 22, wherein the display is selected from the group consisting of an analog display and a digital display.

24. The apparatus of claim 12, further comprising an assembly for translating movement of the first device to the pad.

25. The apparatus of claim 24, wherein the translating assembly operates substantially friction-free.

26. The apparatus of claim 24, wherein the translating assembly includes an inner shaft and an outer shaft, such that the inner shaft operatively engages the pad at one end and the outer shaft at another end.

27. An apparatus for determining a value that correlates to available traction comprising:
   a pad having a first major surface and a second major surface;
   a bracket connected to the second major surface of the pad, the bracket including a bore and a bearing surface;
   an outer shaft including a through-bore and an annular flange having an upper section and a lower section;
   an inner shaft slidably engaging the bore at one end and the through-bore at another end;
   a first bearing assembly disposed contiguous with the bearing surface and the lower section;
   a second bearing assembly disposed contiguous with the upper section;
   a cap connected to the bracket, the cap including a chamber, an opening and a spring pad, an interior surface of the chamber disposed contiguous with the second bearing assembly;
   a biasing assembly disposed contiguous with the spring pad;

a force assembly including an inner surface disposed contiguous with the biasing element;

a first device connected to the through-bore; and a second device operatively connected to the first device that measures a peak amount of break-away torque.

28. The apparatus of claim 27, wherein the pad has a configuration selected from the group consisting of a disc, a ring and a shape symmetrical about a geometric central axis.

29. The apparatus of claim 27, wherein the pad material is selected from the group consisting of natural material, synthetic material, polymer, elastomer, rubber and polyurethane.

30. The apparatus of claim 27, wherein the pad of material has a durometer in the approximate range of 40 to 80 Shore A.

31. The apparatus of claim 27, wherein the pad of material has a durometer that is relative to the desired surface.

32. The apparatus of claim 27, wherein the first device is selected from the group consisting of a lever arm, a torque wrench and a motor.

33. The apparatus of claim 27, wherein the second device is selected from the group consisting of a torque wrench gauge and a strain gauge.

34. The apparatus of claim 27, further comprising a memory for storing one selected from the group consisting of the peak amount of break-away torque and a traction value that correlates to the peak amount of break-away torque.

35. The apparatus of claim 27, wherein the biasing assembly includes a biasing element that is selected from the group consisting of a coil spring, an air spring, a solenoid, helix drive or drive motor.

36. The apparatus of claim 27, further comprising a display operatively connected to the second device for displaying a selected one from the group consisting of the peak amount of break-away torque and a traction value that correlates to the peak amount of break-away torque.

37. The apparatus of claim 36, wherein the display is selected from the group consisting of an analog display and a digital display.

38. The apparatus of claim 27, wherein the force assembly includes a housing connected to a base to facilitate application of a force to overcome the biasing element.

39. The apparatus of claim 38, wherein the base includes a load ring for concentrating contact of the force assembly with the desired surface.

40. The apparatus of claim 39, wherein the load ring includes an inner diameter that is larger than an outer diameter of the pad.

* * * * *